(12) United States Patent
Michel et al.

(10) Patent No.: US 8,648,011 B2
(45) Date of Patent: Feb. 11, 2014

(54) HERBICIDAL COMPOSITIONS

(75) Inventors: Albrecht Michel, Basel (CH); Gavin John Hall, Bracknell (GB); Ian Zlexei Zelaya, Bracknell (GB)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/512,279

(22) PCT Filed: Nov. 23, 2010

(86) PCT No.: PCT/GB2010/002160
§ 371 (c)(1),
(2), (4) Date: Sep. 23, 2012

(87) PCT Pub. No.: WO2011/064533
PCT Pub. Date: Jun. 3, 2011

(65) Prior Publication Data
US 2013/0053242 A1    Feb. 28, 2013

(30) Foreign Application Priority Data
Nov. 27, 2009 (GB) ................... 0920891.9

(51) Int. Cl.
*A01N 25/26* (2006.01)
*A01N 25/32* (2006.01)
*A01N 43/54* (2006.01)

(52) U.S. Cl.
USPC ............................ 504/100; 504/111; 504/243

(58) Field of Classification Search
None
See application file for complete search history.

(56) References Cited

FOREIGN PATENT DOCUMENTS

| WO | 99/66795 | | 12/1999 |
|---|---|---|---|
| WO | WO 9966795 | * | 12/1999 |
| WO | 01/43546 | | 6/2001 |
| WO | WO 0143546 | * | 6/2001 |
| WO | 2002/085120 | | 10/2002 |
| WO | WO 02085120 | * | 10/2002 |
| WO | 2007/042447 | | 4/2007 |
| WO | WO 2007042447 | * | 4/2007 |
| WO | 2008/122395 | | 10/2008 |
| WO | WO 2008122395 | * | 10/2008 |
| WO | 2010/040485 | | 4/2010 |

* cited by examiner

*Primary Examiner* — Alton Pryor
(74) *Attorney, Agent, or Firm* — James Cueva

(57) ABSTRACT

The present invention provides a herbicidal composition comprising:
(i) a compound of Formula (I):

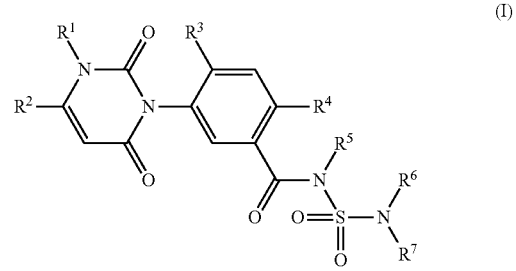

wherein $R^1, R^2, R^3, R^4, R^5, R^6$ and $R^7$ are as defined herein; and
(ii) a safener of Formula (II);

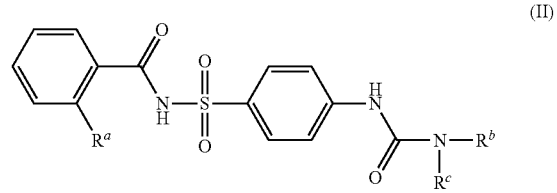

or an agronomically acceptable salt of said compounds, wherein $R^a$, $R^b$ and $R^c$ are as defined herein.

9 Claims, No Drawings

HERBICIDAL COMPOSITIONS

This application is a 371 of International Application No. PCT/GB2010/002160 filed Nov. 23, 2010, which claims priority to GB 0920891.9 filed Nov. 27, 2009, the contents of which are incorporated herein by reference.

The present invention relates to improved herbicidally active compositions comprising herbicidal 3-phenyluracils and certain defined herbicide safeners. The present invention further relates to the use of the improved herbicidal compositions for controlling weeds, in particular in crop plants, which are safer to crop plants (i.e. exhibit less phytotoxicity).

Herbicidal 3-phenyluracils are known in the art, for example as disclosed in WO01/083459. Furthermore, compositions comprising 3-phenyluracils combined with certain herbicide safeners are known in the art, for example as disclosed in WO 2004/080183 and WO2007/042447. However, it has been discovered that these known 3-phenyluracil/safener combinations are not always crop safe insofar as they exhibit unacceptable levels of phytotoxicity in the crops plants. There exists a need therefore to provide improved herbicidal compositions which exhibit reduced crop phytotoxicity—and it has now been discovered that alternative safeners—hitherto not taught in combination with 3-phenyluracil compounds—are surprisingly effective in safening of 3-phenyluracil herbicidal compounds in crop plants.

Thus, according to the present invention there is provided a herbicidal composition comprising:

(i) a compound of Formula (I):

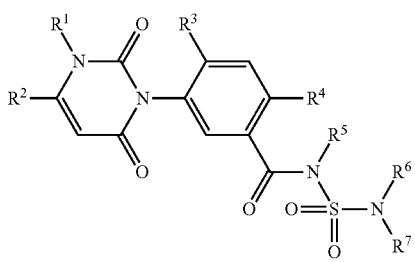

or an agronomically acceptable salt of said compound, wherein:—

$R^1$ is methyl or $NH_2$;
$R^2$ is $C_1$-$C_2$ haloalkyl;
$R^3$ is hydrogen of halogen;
$R^4$ is halogen or cyano;
$R^5$ is selected from the group consisting of hydrogen, cyano, $C_1$-$C_6$ alkyl, $C_1$-$C_6$ alkoxy, $C_1$-$C_4$ alkoxy-$C_1$-$C_4$alkyl, $C_3$-$C_7$ cycloalkyl, $C_3$-$C_6$alkenyl, $C_3$-$C_6$ alkynyl and benzyl which is optionally substituted by halogen and/or $C_1$-$C_6$ alkyl; and
$R^6$ and $R^7$ are independently selected from the group consisting of hydrogen, $C_1$-$C_6$ alkyl, $C_1$-$C_6$ alkoxy, $C_3$-$C_6$ alkenyl, $C_3$-$C_6$ alkynyl, $C_3$-$C_7$ cycloalkyl, $C_3$-$C_7$ cycloalkenyl, phenyl and benzyl, wherein each of the eight above-mentioned substituents is optionally substituted by one to six halogen atoms and/or by one, two or three groups selected from: OH, $NH_2$, CN, $CONH_2$, $C_1$-$C_4$ alkoxy, $C_1$-$C_4$ haloalkoxy, $C_1$-$C_4$ alkylthio, $C_1$-$C_4$ haloalkylthio, $C_1$-$C_4$alkylsulfonyl, $C_1$-$C_4$ haloalkylsulfonyl, $C_1$-$C_4$ alkylamino, di($C_1$-$C_4$-alkyl)amino, formyl, $C_1$-$C_6$ alkylcarbonyl, $C_1$-$C_4$ alkoxycarbonyl, $C_1$-$C_4$ alkylaminocarbonyl, di($C_1$-$C_4$ alkyl)aminocarbonyl, $C_3$-$C_7$ cycloalkyl, phenyl and benzyl; and (ii) a safener of Formula (II);

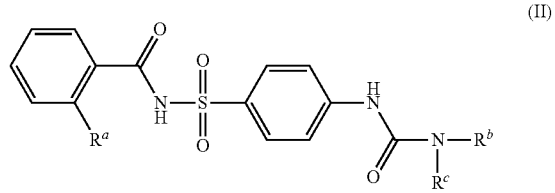

or an agronomically acceptable salt of said compounds, wherein:—

$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, alkoxycarbonyl and $C_1$-$C_4$ alkylcarbonyl; and
$R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

Halogen encompasses fluorine, chlorine, bromine or iodine. The same correspondingly applies to halogen in the context of other definitions, such as haloalkyl. Haloalkyl groups are thus, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl and heptafluoro-n-propyl.

Alkoxy is, for example, methoxy, ethoxy, propoxy, isopropoxy, n-butoxy, isobutoxy, sec-butoxy or tert-butoxy, preferably methoxy and ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

Thus in a preferred embodiment of the present invention, $R^1$ is methyl or $NH_2$, $R^2$ is trifluoromethyl, $R^3$ is selected from the group consisting of hydrogen, fluorine and chlorine, $R^4$ is halogen or cyano, $R^5$ is hydrogen, $R^6$ and $R^7$ are independently selected from the group consisting of hydrogen, $C_1$-$C_6$ alkyl, $C_3$-$C_6$ alkenyl, $C_3$-$C_6$ alkynyl, $C_3$-$C_7$ cycloalkyl, $C_3$-$C_7$ cycloalkenyl, phenyl and benzyl. In a particular preferred embodiment the herbicidal compound of Formula (I) is one in which $R^1$ is methyl, $R^2$ is trifluoromethyl, $R^3$ is fluorine, $R^4$ is chlorine, $R^5$ is hydrogen, $R^6$ is isopropyl and $R^7$ is methyl.

Safeners of Formula (II) are known from EP-A-365484. In a preferred embodiment the safener of is of Formula (II) in which $R^a$ is $C_1$-$C_4$ alkoxy, preferably methoxy; $R^b$ is $C_1$-$C_6$ alkyl, preferably methyl and $R^c$ is hydrogen or methyl. In a particularly preferred embodiment the safener is 1-[4-(N-2-methoxybenzoylsulfamoyl)phenyl]-3-methylurea.

The herbicide: safener ratio in the herbicidal composition may vary depending on the exact nature of the intended application. Typically the ratio will be from 100:1 to 1:100 on a weight for weight basis, preferably from 50:1 to 1:50, more preferably from 25:1 to 1:25 and suitably 1:1.

The herbicidal compositions of the present invention will typically be formulated using in the art recognised formulation adjuvants, such as carriers, solvents and surface-active agents (SFAs). Thus, the present invention further provides a herbicidal composition further comprising an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), suspo-emulsions (SE), aerosols, capsule suspensions (CS) and seed treatment formulations.

The herbicidal composition of the present invention may further comprise at least one additional pesticide, for example a nematicide, an insecticide, a fungicide and/or a herbicide. Examples of suitable pesticides are listed in "The Pesticide Manual", Fourteenth Edition (2006), Editor, C. D. S. Tomlin. Preferably, the additional pesticide is one or more herbicides selected from the group consisting of glyphosate, glufosinate, fomesafen, lactofen, acifluorofen, cafentrazone-ethyl fluthiacet, oxyfluorfen, flumiclorac sulfentrazone, flumioxazin, metolachlor, S-metolachlor, acetochlor, alachlor, pyroxasulfone, flufenacet, dimethenamid, dimethenamid-P, bromoxynil, bentazon, metribuzin, atrazine, terbuthylazine, diuron, fluazifop, clethodim, fenoxaprop, haloxyfop, bensulfuron, nicosulfuron, rimsulfuron, primisulfuron, thifensulfuron, foramsulfuron, chlorsulfuron, halosulfuron, imaziquin, imazapic, imazapic, imazapyr imazethapyr, imazamox, iodosulfuron, metsulfuron, mesosulfuron sulfosulfuron trifloxysulfuron tribenuron methyl, thiazopyr, tebuthiuron, cloransulam-methyl, flucarbazone, flumetsulam amicarbazone, thiencarbazone, chlorimuron-ethyl, dicamba, 2,4-D, 2,4-DB, fluoroxypyr, diflufenzopry, tirclopry, picloram, quinclorac, clopyralid and aminopyralid; or agrochemically acceptable salts thereof. The herbicidal composition applied to the locus may also further comprise an additional herbicide safener.

The present invention still further provides a method of selectively controlling weeds at a locus comprising crop plants and weeds, wherein the method comprises application to the locus of a weed controlling amount of:

(i) a compound of Formula (I):

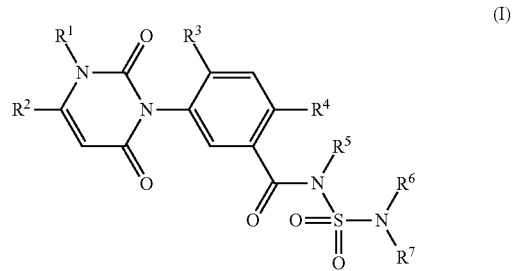

or an agronomically acceptable salt of said compound, wherein:—

$R^1$ is methyl or $NH_2$;
$R^2$ is $C_1$-$C_2$ haloalkyl;
$R^3$ is hydrogen of halogen;
$R^4$ is halogen or cyano;
$R^5$ is selected from the group consisting of hydrogen, cyano, $C_1$-$C_6$ alkyl, $C_1$-$C_6$ alkoxy, $C_1$-$C_4$ alkoxy-$C_1$-$C_4$alkyl, $C_3$-$C_7$ cycloalkyl, $C_3$-$C_6$alkenyl, $C_3$-$C_6$ alkynyl and benzyl which is optionally substituted by halogen and/or $C_1$-$C_6$ alkyl; and
$R^6$ and $R^7$ are independently selected from the group consisting of hydrogen, $C_1$-$C_6$ alkyl, $C_1$-$C_6$ alkoxy, $C_3$-$C_6$ alkenyl, $C_3$-$C_6$ alkynyl, $C_3$-$C_7$ cycloalkyl, $C_3$-$C_7$ cycloalkenyl, phenyl and benzyl, wherein each of the eight above-mentioned sustituents is optionally substituted by one to six halogen atoms and/or by one, two or three groups selected from: OH, $NH_2$, CN, $CONH_2$, $C_1$-$C_4$ alkoxy, $C_1$-$C_4$ haloalkoxy, $C_1$-$C_4$ alkylthio, $C_1$-$C_4$ haloalkylthio, $C_1$-$C_4$alkylsulfonyl, $C_1$-$C_4$ haloalkylsulfonyl, $C_1$-$C_4$ alkylamino, di($C_1$-$C_4$-alkyl)amino, formyl, $C_1$-$C_6$ alkylcarbonyl, $C_1$-$C_4$ alkoxycarbonyl, $C_1$-$C_4$alkylaminocarbonyl, di($C_1$-$C_4$alkyl)aminocarbonyl, $C_3$-$C_7$ cycloalkyl, phenyl and benzyl; and (ii) a safener of Fomula (II);

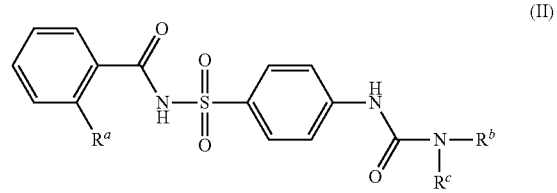

or an agronomically acceptable salt of said compounds, wherein:—

$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and $R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

Controlling' means killing, reducing or retarding growth or preventing or reducing germination. Generally the plants to be controlled are unwanted plants (weeds). 'Locus' means the area in which the plants are growing or will grow.

Components (i) and (ii) can be independently applied to the locus pre-planting, pre-emergence and/or post emergence.

By "pre-planting" it is meant that the herbicidal composition is applied before the crop is planted at the locus, by "pre-emergence" it is meant that the herbicidal composition is applied before the germinating crop plant seed emerges above the locus surface and by "post-emergence" it is meant that the herbicide composition is applied once the crop plant is visible above the locus surface. Component (ii) may also be applied to seed as a seed treatment prior to sowing optionally followed by a combined application of components (i) and (ii). Typically, and in a preferred embodiment, component (i) and (ii) will be applied to the locus in a single combined pre or post-emergence application.

The rates of application of components (i) and (ii) will vary depending on the particular application (e.g. method of application (pre- or post-emergence; seed dressing; application to the seed furrow; no tillage application etc.), the crop plant, the weed(s) to be controlled, the prevailing climatic conditions, and other factors governed by the method of application, the time of application and the target crop). Typically, the rate of application of herbicide (i) will be from 10 to 500 g ha, suitably from 10 to 250 g/ha. The rate of application of the safener component (ii) is suitably from 5 to 500 g/ha, more suitably from 10 to 100 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet and sugar cane. Maize is however particularly preferred. Crop plants can also include turf and trees, such as fruit trees, palm trees, coconut trees or other nuts. Also included are vines such as grapes, fruit bushes, fruit plants and vegetables. It should be understood that the crop plants also include those which have been genetically engineered so as to be tolerant to one or more additional herbicides, insects, fungal, bacterial and/or viral infections. Examples are crop plants which comprise glyphosate tolerant 5-enol-pyruvylshikimate-3-phosphate synthase (EPSPS) (for example as disclosed in U.S. Pat. No. 5,804,425, U.S. Pat. No. 6,566,587), glyphosate N-acetyl transferase (GAT) (for example as disclosed in WO02/036782), herbicide tolerant 4-hydroxypyruvyldioxygenase (HPPD) (for example as disclosed in WO02/46387), phosphinothricin acetyl transferase (PAT) (for example as disclosed in U.S. Pat. No. 5,273,894), cytochrome P450 (for example as disclosed in WO 07/103,567), glutathione S-transferase (GST) (for example as disclosed in WO01/21770), herbicide tolerant acetyl-COA-carboxylase (ACCase), herbicide tolerant aceto-lactate synthase (ALS) (for example as disclosed in U.S. Pat. No. 5,013,659), herbicide tolerant protoporphyrinogen oxidase (PPGO) (for example as disclosed in WO95/34659), bromoxynil nitrilase (for example, as disclosed in WO89/00193), herbicide tolerant phytoene desaturase (for example as disclosed in EP0393690), aryloxyalkanoate dioxygenase (for example as disclosed in WO2005/107437 and WO2007/053482) and dicamba degrading enzymes (for example as disclosed in WO98/45424); including known mutagenised or otherwise modified variants of these polypeptides.

The compositions can be used to control unwanted plants (collectively, 'weeds'). The weeds to be controlled may be both monocotyledonous species, for example Agrostis, Alopecurus, Avena, Bromus, Cyperus, Digitaria, Echinochloa, Lolium, Monochoria, Rottboellia, Sagittaria, Scirpus, Setaria, Sida and Sorghum, and dicotyledonous species, for example Abutilon, Amaranthus, Chenopodium, Chrysanthemum, Conyza, Galium, Ipomoea, Nasturtium, Sinapis, Solanum, Stellaria, Veronica, Viola and Xanthium. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

BIOLOGICAL EXAMPLES

A glass house test was carried out to determine the safening effect of numerous safeners on a compound of Formula (I) with respect to maize. Various herbicidal compositions were applied post-emergence and the observed phytotoxicity in maize assessed 24 days after application (24DAA). A=2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide; B=1-[4-(N-2-methoxybenzoylsulfamoyl)phenyl]-3-methylurea. The results are summarised in Table 1 below and indicate that safener B provides surprisingly good safening of the 3-phenyluracil herbicide A in maize.

TABLE 1

| Herbicde | Rate g/ha | Safener | Rate g/ha | Phytotoxicity (%) |
|---|---|---|---|---|
| A | 100 g/ha | — | 100 g/ha | 25 |
| A | 250 g/ha | — | 250 g/ha | 35 |
| A | 100 g/ha | Benoxacor | 100 g/ha | 28 |
| A | 250 g/ha | | 250 g/ha | 28 |
| A | 100 g/ha | Cloquintocet | 100 g/ha | 25 |
| A | 250 g/ha | | 250 g/ha | 35 |
| A | 100 g/ha | Isoxadifen | 100 g/ha | 28 |
| A | 250 g/ha | | 250 g/ha | 30 |
| A | 100 g/ha | Fluxofenim | 100 g/ha | 35 |
| A | 250 g/ha | | 250 g/ha | 50 |
| A | 100 g/ha | Mefenpyr | 100 g/ha | 30 |
| A | 250 g/ha | | 250 g/ha | 40 |
| A | 100 g/ha | Cyprosulfamide | 100 g/ha | 5 |
| A | 250 g/ha | | 250 g/ha | 10 |
| A | 100 g/ha | B | 100 g/ha | 0 |
| A | 250 g/ha | | 250 g/ha | 0 |

The invention claimed is:

1. A herbicidal composition comprising:
(i) a compound of Formula (I):

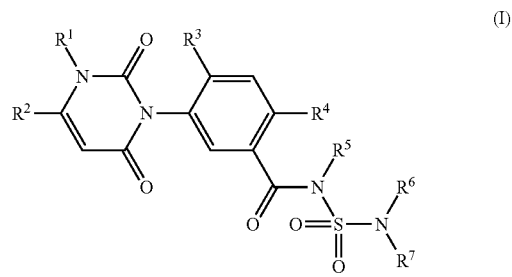

or an agronomically acceptable salt of said compound, wherein:—
$R^1$ is methyl or $NH_2$;
$R^2$ is $C_1$-$C_2$ haloalkyl;
$R^3$ is hydrogen or halogen;
$R^4$ is halogen or cyano;
$R^5$ is selected from the group consisting of hydrogen, $C_1$-$C_6$ alkyl, $C_1$-$C_4$ alkoxy-$C_1$-$C_4$alkyl, $C_3$-$C_6$alkenyl and $C_3$-$C_6$ alkynyl; and $R^6$ and $R^7$ are independently selected from the group consisting of hydrogen, $C_1$-$C_6$ alkyl, $C_3$-$C_6$ alkenyl, $C_3$-$C_6$ alkynyl, wherein each of the above-mentioned $R^6$ and $R^7$ sustituents is optionally substituted by one to six halogen atoms and/or by one, two or three groups selected from: OH, $NH_2$, CN, $CONH_2$, $C_1$-$C_4$ alkoxy, $C_1$-$C_4$ haloalkoxy, $C_1$-$C_4$ alkylthio, $C_1$-$C_4$ haloalkylthio, $C_1$-$C_4$alkylsulfonyl, $C_1$-$C_4$ haloalkylsulfonyl, $C_1$-$C_4$ alkylamino, di($C_1$-$C_4$-alkyl)amino, formyl, $C_1$-$C_6$ alkylcarbonyl, $C_1$-$C_4$ alkoxycarbonyl, $C_1$-$C_4$ alkylaminocarbonyl, di($C_1$-$C_4$ alkyl)aminocarbonyl, $C_3$-$C_7$ cycloalkyl; and (ii) a safener of Formula (II);

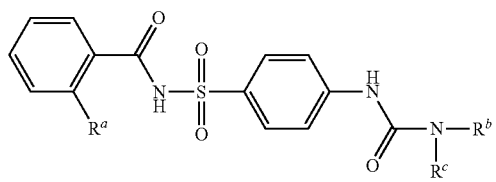

or an agronomically acceptable salt of said safener compound, wherein:—
$R^a$ is selected from the group consisting of $C_1$-$C_4$ haloalkoxy, $C_1$-$C_4$ alkoxy, and $C_1$-$C_4$ alkylthio; and $R^b$ and $R^c$ are independently selected from the group consisting of hydrogen, $C_1$-$C_6$ alkyl, $C_3$-$C_6$ alkenyl and $C_3$-$C_6$ alkynyl.

2. A herbicidal composition accordingly to claim 1, wherein:
$R^1$ is methyl or $NH_2$;
$R^2$ is trifluoromethyl;
$R^3$ is selected from the group consisting of hydrogen, fluorine and chlorine;
$R^4$ is halogen or cyano;
$R^5$ is hydrogen;
$R^6$ and $R^7$ are independently selected from the group consisting of hydrogen, $C_1$-$C_6$ alkyl, $C_3$-$C_6$ alkenyl, and $C_3$-$C_6$ alkynyl.

3. A herbicidal composition according to claim 2, wherein
$R^1$ is methyl;
$R^2$ is trifluoromethyl;
$R^3$ is fluorine;
$R^4$ is chlorine;
$R^5$ is hydrogen;
$R^6$ is isopropyl; and
$R^7$ is methyl.

4. A herbicidal composition according to claim 1, wherein the safener is a compound of Formula (II) wherein:—
$R^a$ is $C_1$-$C_4$ alkoxy;
$R^b$ is $C_1$-$C_6$ alkyl; and
$R^c$ is hydrogen.

5. A herbicidal composition according to claim 1, further comprising at least one additional pesticide.

6. A method of selectively controlling weeds in crop plants at a locus comprising crop plants and weeds, wherein the method comprises applying to the locus of a weed controlling amount of:

(i) a compound of Formula (I):

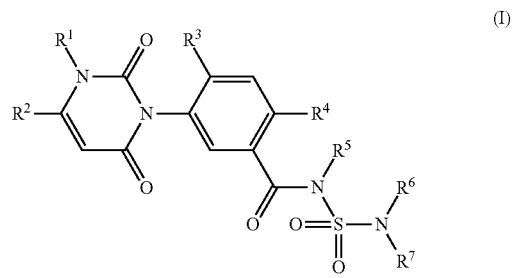

or an agronomically acceptable salt of said compound, wherein:—
$R^1$ is methyl or $NH_2$;
$R^2$ is $C_1$-$C_2$ haloalkyl;
$R^3$ is hydrogen or halogen;
$R^4$ is halogen or cyano;
$R^5$ is selected from the group consisting of hydrogen, $C_1$-$C_6$ alkyl, $C_1$-$C_4$ alkoxy-$C_1$-$C_4$alkyl, $C_3$-$C_6$alkenyl and $C_3$-$C_6$ alkynyl; and
$R^6$ and $R^7$ are independently selected from the group consisting of hydrogen, $C_1$-$C_6$ alkyl, $C_3$-$C_6$ alkenyl, $C_3$-$C_6$ alkynyl, wherein each of the above-mentioned $R^6$ and $R^7$ sustituents is optionally substituted by one to six halogen atoms and/or by one, two or three groups selected from: OH, $NH_2$, CN, $CONH_2$, $C_1$-$C_4$ alkoxy, $C_1$-$C_4$ haloalkoxy, $C_1$-$C_4$ alkylthio, $C_1$-$C_4$ haloalkylthio, $C_1$-$C_4$alkylsulfonyl, $C_1$-$C_4$ haloalkylsulfonyl, $C_1$-$C_4$ alkylamino, di($C_1$-$C_4$-alkyl)amino, formyl, $C_1$-$C_6$ alkylcarbonyl, $C_1$-$C_4$ alkoxycarbonyl, $C_1$-$C_4$ alkylaminocarbonyl, di($C_1$-$C_4$ alkyl)aminocarbonyl, $C_3$-$C_7$ cycloalkyl; and (ii) a safener of Formula (II);

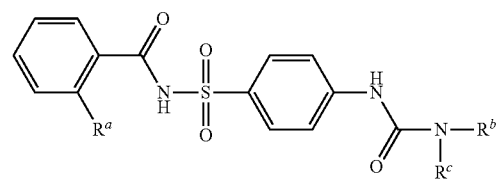

or an agronomically acceptable salt of said safener compound, wherein:—
$R^a$ is selected from the group consisting of halogen, nitro, $C_1$-$C_4$ alkyl, $C_1$-$C_4$ haloalkyl, $C_1$-$C_4$ haloalkoxy, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and $R^b$ and $R^c$ are independently selected from the group consisting of hydrogen, $C_1$-$C_6$ alkyl, $C_3$-$C_6$ alkenyl and $C_3$-$C_6$ alkynyl; and
wherein the crop plant is selected from the group consisting of barley, wheat, maize, rice, sugar cane and turf.

7. A method according to claim 6, wherein the crop plant is maize.

8. A method according claim 6, wherein component (ii) is also applied as a seed treatment to the crop plant prior to sowing.

9. A method according to claim 6, wherein components (i) and (ii) are applied to the locus as a single, post-emergence application.

* * * * *